United States Patent [19]
Drolet et al.

[11] Patent Number: 5,789,163
[45] Date of Patent: Aug. 4, 1998

[54] ENZYME LINKED OLIGONUCLEOTIDE ASSAYS (ELONAS)

[75] Inventors: Dan W. Drolet; Sumedha D. Jayasena; Larry Gold, all of Boulder, Colo.

[73] Assignee: NeXstar Pharmaceuticals, Inc., Boulder, Colo.

[21] Appl. No.: 487,425

[22] Filed: Jun. 7, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and a continuation-in-part of Ser. No. 964,624, Oct. 21, 1992, Pat. No. 5,496,938, and a continuation-in-part of Ser. No. 233,012, Apr. 25, 1994, and a continuation-in-part of Ser. No. 234,997, Apr. 28, 1994, Pat. No. 5,683,867.

[51] Int. Cl.⁶ .............. C12Q 1/68; C12P 19/34; G01N 33/53; G01N 33/537

[52] U.S. Cl. .............. 435/6; 435/91.2; 435/7.1; 435/7.4; 435/7.5; 435/7.9; 435/7.92; 935/77; 935/78

[58] Field of Search .............. 435/6, 91.2, 7.1, 435/7.4, 7.5, 7.9, 7.92; 935/77, 78

[56] References Cited

U.S. PATENT DOCUMENTS 5,459,015  10/1995  Janjic et al. .............. 435/6

FOREIGN PATENT DOCUMENTS

| | | | |
|---|---|---|---|
| 2 183 661 | 6/1987 | United Kingdom . | |
| WO 89/06694 | 7/1989 | WIPO . | |
| 9214843 | 9/1992 | WIPO .............. | 435/6 |
| WO 93/05182 | 3/1993 | WIPO . | |
| WO 94/01448 | 1/1994 | WIPO . | |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Hendrickson et al. (1995) NAR 23:522.
Hibma et al. (1994) NAR 22:3806.
Kinzler and Vogelstein (1989) Nucleic Acids Research 17:3645.
Kramer et al. (1974) J. mol. Biol. 89:719.
Levisohn et al. (1969) PNAS 63:805.
Levisohn et al. (1969) PNAS 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

This invention discloses novel immunoassay termed an ELONA, employing nucleic acid ligands as capture molecules and/or detector molecules.

23 Claims, 3 Drawing Sheets

1

ENZYME LINKED OLIGONUCLEOTIDE ASSAYS (ELONAS)

RELATED APPLICATIONS

This application is a Continuation-in-Part of U.S. patent application Ser. No. 07/714,131, filed Jun. 10, 1991, entitled "Nucleic Acid Ligands", now U.S. Pat. No. 5,475,096 which is a Continuation-in Part of U.S. patent application Ser. No. 07/536,428, filed Jun. 11, 1990, entitled "Systematic Evolution of Ligands by Exponential Enrichment", now abandoned, U.S. patent application Ser. No. 07/964,624, filed Oct. 21, 1992, entitled "Methods of Producing Nucleic Acid Ligands," now U.S. Pat. No. 5,496,938 U.S. patent application Ser. No. 08/233,012, filed Apr. 25, 1994, entitled "High Affinity Oligonucleotide Ligands to Vascular Endothelial Growth Factor (VEGF)," and U.S. patent application Ser. No. 08/234,997, filed Apr. 28, 1994, entitled "Systematic Evolution of Ligands by Exponential Enrichment: Blended SELEX", now U.S. Pat. No. 5,683,867.

FIELD OF INVENTION

Described herein are methods for performing a novel immunoassay employing nucleic acid ligands as capture and/or detector molecules. The method utilized herein for identifying and preparing said nucleic acid ligands is called SELEX, an acronym for Systematic Evolution of Ligands by EXponential enrichment. The invention includes high-affinity nucleic acid ligands which bind to various targets which can act as capture molecules and/or detector molecules in a sandwich type ELISA format for the detection of targets in biological fluids, cell culture media and industrial processes and further determination of the target quantity found in the substance. Specifically disclosed are assays wherein nucleic acid ligands to human vascular endothelial growth factor (VEGF), human chorionic gonadotropin (hCG) and human thyroid stimulating hormone (hTSH) are used to capture and/or to detect the captured target compound.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands" now U.S. Pat. No. 5,475,096, U.S. patent application Ser. No. 07/931,473, filed Aug. 17, 1992, entitled "Nucleic Acid Ligands", now U.S. Pat. No. 5,270,163 (see also WO 91/19813, each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" now U.S. Pat. No. 5,496,938 describes methods for obtaining improved nucleic acid ligands after SELEX has been performed. U.S. patent application Ser. No. 08/400, 440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement", describes methods for making various 2'-modified nucleosides.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Without question, the SELEX process is very powerful. The nucleic acid ligands obtained by the SELEX process have the ability to act in many capacities. One of the capacities that nucleic acid ligands possess is the ability to bind specifically to a target.

Specific and high affinity molecular recognition is critical for diagnostic applications. Until recently, engineering of molecules that recognize targets has been mainly limited to proteins. Protein molecules that recognize a specific target have typically been generated as antibodies. As a result, antibodies have received a central role in the development of analytical and separation methods that are currently being used. The methods which primarily use antibodies include, immunometric assays, such as enzyme-linked immunosorbent assays (ELISAs), radioimmunoassays, flow cytometry diagnostics, blotting applications, fluorescent anisotropy, membrane assays, biosensors, etc.

Immunometric assays have been found to be particularly well suited for the detection of polyvalent targets or antigens, ie., antigenic substances that are able to complex with two or more antibodies at the same time. Such assays typically employ a quantity of unlabelled antibody bound to a solid support that is insoluble in the fluid being tested and a quantity of soluble antibody bearing a label such as an enzyme or a radioactive isotope that permits detection and/or a quantitative estimate of the ternary complex formed between solid phase antibody, antigen and labelled antibody. Details regarding immunometric assays are provided in U.S. Pat. No. 4,486,530.

An ELISA is a highly sensitive immunoassay method, with excellent minimum limits of detection, in which an antigen is detected by means of an enzyme chemically coupled to an antibody specific for the antigen (the detector molecule). Typically, a capture molecule is attached to a solid support. A substance which may contain a target compound is applied and allowed to react with the capture molecule and form a capture molecule:target complex. After washing, a detector molecule is added to react with the target to form a capture molecule:target complex:detector molecule complex. Finally, the detection system (an enzyme-linked to the detector molecule) indicates that an interaction has occurred and the complex has been formed. The amount of detector molecule bound in the complex is subsequently measured by addition of a substrate for an enzyme which develops a color when hydrolyzed. Commonly used enzymes are horseradish peroxidase or alkaline phosphatase. The target or antigen is, thus, "sandwiched" between the two layers of molecules, traditionally antibodies. This technique is employed in an ELISA procedure and is adaptable to the ELONA procedure described herein.

In addition to antibodies, oligonucleotides are also being used in diagnostics, but in a different manner. Sequence information of oligonucleotide probes is used to specifically target genomic complementary base sequences in techniques such as Southern blotting, in situ hybridization and polymerase-based amplifications. However, information stored in an oligonucleotide is not being generally used to detect non-nucleic acid molecules. The information content (linear sequence) of nucleic acids relies on Watson/Crick base pairing and can only discriminate among DNAs. However, relying on structural content (three-dimensional structures), nucleic acid ligands can be used in diagnostic applications for any type of target. Before SELEX, the structural content of nucleic acids was essentially not appreciated and there was no way to utilize the structural capabilities of nucleic acids.

The use of nucleic acid ligands in diagnostic assays which were previously believed to depend on antibody recognition has not been demonstrated so far. The present invention demonstrates that SELEX-derived oligonucleotides that bind with high affinity to human VEGF, hCG and hTSH can replace the traditional use of an antibody in a sandwich ELISA format.

SUMMARY OF INVENTION

The present invention includes methods of performing novel immunoassays employing nucleic acid ligands. More specifically, the present invention includes a novel sandwich-type Enzyme-Linked OligoNucleotide Assay (ELONA) procedure employing novel nucleic acid ligands as the capture and/or detector molecules.

The present invention provides a method for detecting the presence of a target compound in a substance which may contain said target compound comprising a) exposing a substance which may contain said target compound to a capture molecule capable of binding to said target molecule; b) removing the remainder of said substance from said capture molecule:target molecule complex; c) adding to said capture molecule:target molecule complex a detector molecule capable of binding to said target molecule; and d) detecting said capture molecule:target molecule:detector molecule complex; wherein said capture molecule, detector molecule or both are a nucleic acid ligand to said target molecule.

More specifically, the ELONAs of the present invention are useful for detecting VEGF, hCG, and hTSH.

DETAILED DESCRIPTION OF THE INVENTION

Figure 1:
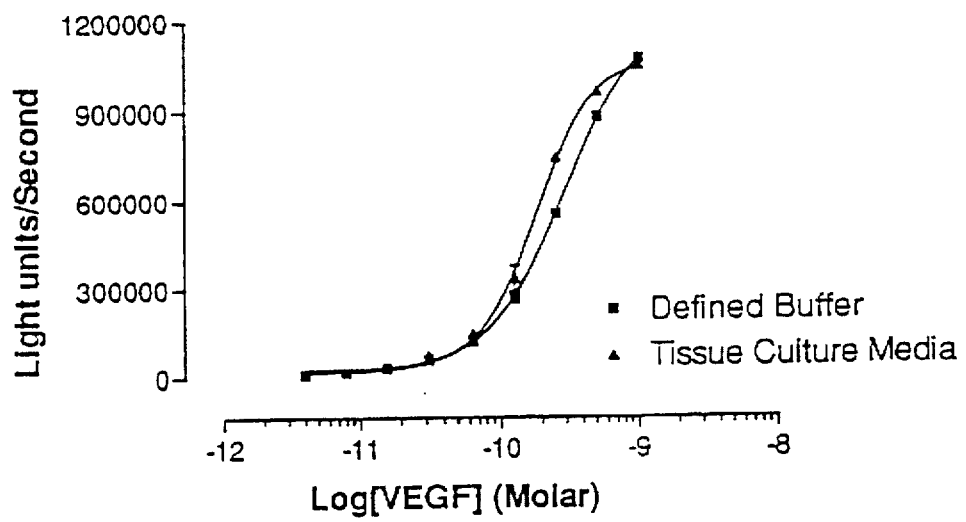
FIG. 1 shows typical standard curves obtained for VEGF detection by ELONA in either a defined binding buffer or using tissue culture media [DME high glucose, 10% fetal bovine serum (FBS)].

This application describes the use of high-affinity nucleic acid ligands to various targets in immunoassay protocols.

Nucleic acid ligand is defined herein as a non-naturally occurring nucleic acid having a specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the preferred embodiments, the nucleic acid ligand is a single stranded nucleic acid ligand.

In the preferred embodiment, the nucleic acid ligands are identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now U.S. Pat. No. 5,475,096 U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with a lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. Affinities of SELEX-derived nucleic acid ligands often lie in the same range observed with structurally large monoclonal antibodies.

In one embodiment, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

Until recently, the design and production of biopolymers capable of molecular recognition has been mainly limited to proteins (antibodies). However, SELEX allows the identification of nucleic acid sequences that recognize target molecules with high affinity and specificity. This process is faster than the generation of monoclonal antibodies and does not require the use of animals as required to generate antibodies. Once the sequence of a high-affinity ligand is identified, the material can be chemically synthesized in large quantities. This is a definite advantage over processing and storage of antibody-producing cell lines.

Additionally, specific and high-affinity nucleic acid ligands can be generated for targets that are not readily immunogenic. This adds a new dimension to the types of information that can be gained from this diagnostic application. Clearly, target compounds that have never before been identified can be found using this new procedure.

The nucleic acid ligands of the present invention offer additional advantages over antibodies. Nucleic acid ligands may have a greater specificity for target compounds than the specificity exhibited by conventional antibodies as demonstrated in U.S. patent application Ser. No. 09/134,028, filed Oct. 7, 1993, entitled "High Affinity Nucleic Acid Ligands the Discriminate Between Theophylline and Caffeine," which is herein incorporated by reference. Whereas antibodies generally have multiple binding sites, only two of which are specific for a target compound, the entire molecule of the nucleic acid ligand may be utilized for the binding of a target compound. The nucleic acid ligands of the invention are identified and prepared to contain a single specific binding site. Thus, there is potentially far less nonspecific binding of nontarget compounds when nucleic acid ligands are utilized in immunoassays. This provides a more reliable detection signal for the presence of target compound.

One of the biggest advantages is that the relatively small oligonucleotides of known sequence can easily be replicated in many laboratories and, unlike antibodies, will have the same binding properties. Further, the oligonucleotides can be easily modified to include not only biotins, but other equally useful moieties such as fluorochromes such as fluorescein, radioisotopes such as phosphorous 32 ($^{32}$P), steroids such as cholesterol or digoxygenin and peptides. The various modifications allow the choice of an available reporter system. In fact, it should be possible to covalently or even non-covalently link the oligonucleotide directly to a reporter enzyme such as horseradish peroxidase, alkaline phosphatase or β-galactosidase, among others.

An additional advantage of utilizing nucleic acid ligands in immunoassays is that certain target compounds will bind to nucleic acid ligands, but will not bind to antibodies. Examples of such compounds are small molecules that cannot be conjugated to larger proteins to illicit an immune response in mice or rabbits such as glucose, and catecholamines such as epinephrine, norepinephrine and α-3-deoxy-D-manno-octulosonic acid (a trisaccharide specific for Chlamydia organisms).

Furthermore, due to the smaller size (compared to antibodies), nucleic acid ligands are expected to be effective in intracellular staining, i.e., nucleic acid ligands can be used in detecting the expression of target molecules at the cellular level.

Often, immunoassays are in a sandwich-type format. In a sandwich assay, typically, a capture molecule is attached to a solid support. A substance which may contain a target compound is applied and allowed to react with the capture molecule. After washing, a detector molecule is added to react with the target and the detection system indicates that an interaction has occurred. The target or antigen is, thus, "sandwiched" between the two layers of molecules, traditionally antibodies. This technique is employed in an ELISA procedure and is adaptable to the ELONA procedure described herein. Unless used in a homogeneous detection assay, such as fluorescence anisotropy, most widely used sandwich assays are based on the binding of two molecules, a detector molecule and a capture molecule, to an analyte or target.

The present invention provides a method for detecting the presence of a target compound in a substance which may contain said target compound comprising a) exposing a substance which may contain said target compound to a capture molecule capable of binding to said target molecule; b) removing the remainder of said substance from said capture molecule:target molecule complex; c) adding to said capture molecule:target molecule complex a detector molecule capable of binding to said target molecule; and d) detecting said capture molecule:target molecule:detector molecule complex; wherein said capture molecule, detector molecule or both are a nucleic acid ligand to said target molecule.

The capture molecule and/or the detector molecule must be a nucleic acid ligand to fall within the scope of the present invention. However, it is not required that both the capture molecule and the detector molecule be nucleic acid ligands. The ability of nucleic acid ligands to bind a target simultaneously with anti-target antibodies allows the development of a sandwich assay in which the nucleic acid ligand can be used as a capture and an anti-target antibody or a nucleic acid ligand can be used as a detector. In another embodiment, the nucleic acid ligand can be used as the detector molecule, with either a nucleic acid ligand or an antibody being used as the capture molecule. When either the capture molecule or the detector molecule is not a nucleic acid ligand it can be an antibody or other molecule that has specific recognition for the target molecule. In the most preferred embodiment of the invention, both the capture molecule and the detector molecule are nucleic acid ligands.

The capture molecule must bind to the target molecule to form a capture molecule:target molecule complex. The detector molecule must also bind to the target molecule, but additionally must comprise a detection system wherein a capture molecule:target molecule:detector molecule complex can be identified. The detector molecule comprises a detection system which comprises a wide array of known chemical entities. The detection system can be an enzyme, a fluorophore, a radiolabel, etc. The various detection systems are well known to those skilled in the art. In the preferred embodiment, the detector molecule comprises an enzyme.

The attachment of a suitable detection system such as an enzyme or a fluorophore to nucleic acid ligands is not a potential problem and in some cases (fluorophores) they can be attached during the chemical synthesis of the ligand itself. The use of bioluminescent and chemiluminescent substrates allows the detection of AP concentrations in the $10^{-15}$–$10^{-19}$M range. The sensitivity of this assay can be further increased by using bioluminescence or chemiluminescence when nucleic acid ligands are attached to alkaline phosphatase (AP).

In another embodiment, the detection system can be PCR amplification of the nucleic acid ligand which is a part of the capture molecule:target molecule:detector molecule complex. PCR amplification methods are well known to those skilled in the art. In this embodiment, the PCR primers used for amplication can also comprise various reporter molecules. The reporter molecules can be enzymes, biotins, or other known reporter groups.

The preferred use of the ELONAs of the present invention is for the detection of target compounds for the clinical diagnosis of physiologic conditions, the immunoassays will most frequently be contacted with a substance which may contain a target compound. The substance is usually a biological material which may or may not contain the target compound of interest. Such biological materials include blood, plasma, serum, sputum, urine, semen, cerebrospinal fluid, bronchial aspirate, and macerated tissue. The ELONAs of the present invention are useful for both human and veterinary diagnostics. Other samples which may be assayed with the ELONAs of the invention include foods and environmental discharges such as liquid wastes.

In Example 1, an RNA ligand with specific high affinity for hVEGF was used in a sandwich-type ELONA procedure. The assay described herein was performed using, as the capture molecule, a monoclonal antibody against hVEGF (R&D systems) bound to the solid surface of a microtiter plate. For the detector molecule, a hVEGF-binding biotinylated nucleic acid ligand was used. After a final incubation with alkaline phosphatase labeled streptavidin, signal was generated using a chemiluminescent alkaline phosphatase detection system (Tropix, Inc. (Bedford, Mass.)). The practical minimum detection limit for VEGF was 4 picomolar and the relative standard deviation ranged from 1 to 10%. Standard curves can be performed in a defined buffer, tissue culture media or plasma. The results obtained compare favorably to other published VEGF ELISA's demonstrating that SELEX derived ligands represent a viable alternative to the use of antibodies in clinical assays.

In Examples 2 and 3, an RNA ligand with high affinity for hCG or hTSH, respectively, was used in a sandwich-type ELONA procedure. The assay described herein was performed using, as the capture molecule, the hCG or hTSH nucleic acid ligand which was conjugated to biotin and bound to the surface of a streptavidin-coated microtiter plate. For the detector molecule, an hCG-specific or hTSH-specific detector antibody labelled with horseradish peroxidase was used.

EXAMPLE 1

VEGF ELONA

Vascular endothelial growth factor (VEGF) is a potent angiogenic factor that has been implicated as vital for the growth and metastasis of certain solid tumors (Kim et al., 1993 Nature 362:841–844). Thus VEGF plasma levels may be clinically important for determining a course of cancer therapy. A SELEX derived oligonucleotide that binds to human VEGF with a $K_d$ of 10 nM (Jellinek, et al., 1994 Biochemistry 33:10450–10456), can act as a detector molecule in a sandwich type ELONA format to detect VEGF levels in tissue culture media and plasma. The VEGF nucleic acid ligand was prepared as described in U.S. patent application Ser. No. 08/233,012, filed Apr. 25, 1994, entitled "High Affinity Oligonucleotide Ligands to Vascular Endothelial Growth Factor (VEGF)," which is incorporated herein by reference.

A. Materials and Methods

Luminometry

Light emission was measured with a Berthold (Nashua, N.H.) LB 96P luminometer. Light emission from individual wells was integrated over 1 second. Luminescent levels were obtained three times with five minute intervals between readings. The set with the highest light emission was used. Microtiter plates (Lumino Combiplate 8) were obtained from Labsystems (Needham Heights, Mass.).

Alkaline Phosphatase conjugated Streptavidin and chemiluminescent substrate

CSPD, "Sapphire" enhancer and the alkaline phosphatase conjugated streptavidin (AVIDx-AP) were obtained from Tropix, Inc., (Bedford, Mass.).

Detect Reagent

The detect reagent consisted of a SELEX derived RNA nucleic acid ligand containing a 3'-Biotin synthesized by standard cyanoethyl phosphoramidite chemistry. This ligand contained 2'NH2-Pyrimidines and contained the following sequence; 5'-ACCCTGATGGTAGACGCCGGG-3'. (SEQ ID NO: 1) This oligonucleotide (VEGF-NeXamer) specifically binds to VEGF.

VEGF and Antibody

Recombinant human VEGF and the monoclonal anti-human VEGF antibody (clone: 26503.11) were obtained from R&D Systems (Minneapolis, Minn.).

Assay Buffers

Coating buffer pH 9.6 consisted of 0.0128M $Na_2CO_3$ and 0.035M $NaHCO_3$. Blocking buffer containing 5 g/L I-block (Tropix, Inc.) was made fresh each week and consisted of phosphate buffered saline (PBS) pH 7.4, 1 mM EDTA and Casein (I-Block). Wash buffer was the same as blocking buffer except it contained 500 µl/L Triton-X 100 (Sigma Chemical Co.; St. Louis, Mo.) and 2 g/L I-block. Assay buffer was made according to manufacturers recommendation (Tropix, Inc.) and consisted of 0.1M diethanolamine, 1 mM $MgCl_2$ and 0.02% sodium azide. TBS was made as 20 mM Tris-HCl pH 7.5, 140 mM sodium chloride and 2.7 mM potassium chloride.

B. ELONA Procedure

All assay procedures were performed at room temperature. Wells were coated overnight with 50 µl of a 10 µg/ml solution of the monoclonal antibody in PBS. The following day the solution was removed, the wells washed once with blocking buffer (100 µl) and then blocked by the addition of blocking buffer (150 µl I-block; Tropix) to the wells for at least 1 hour. Alternatively the wells were simply blocked with Pierce Block (Pierce Chemical Co.) according to the manufacturers' recommendations. After the blocking step, the wells were washed once with wash buffer (100 µl) followed by the addition of serially diluted VEGF standards and test samples appropriately diluted in either wash buffer, rat plasma or tissue culture media. Following a one to four hour incubation, the wells were washed two or three times with wash buffer (150 µl/well) and 50 µl of a 400 nM solution of Biotinylated VEGF-NeXamer in wash buffer was added to each well. After a one hour incubation, the wells were washed as before except with TBS. Alkaline Phosphatase conjugated streptavidin (50 µl/well; 1:1000 dilution in TBS) was then added and allowed to incubate for 30 to 60 minutes. Following a final wash as previously described with 1× TBS, each well received 100 µl of enhancer/substrate (Tropix) solution prepared according to the manufacturer's recommendation. After a 20 minute incubation in the dark, the chemiluminescence was determined.

Data were fit to a four-parameter logistic equation:

$$Y = \text{Bottom} + [(\text{Top}-\text{Bottom})/1+10^{(Log EC50-X)(Hillslope)}]$$

using GraphPad Prism (GraphPad Software; San Diego, Calif.). Each replicate was considered individually and convergence was obtained when two consecutive iterations varied the sum of squares (actual distance of the points from the curve) by less than 0.01%.

FIG. 1 shows typical standard curves obtained in either a defined binding buffer or using tissue culture media (DME high glucose, 10% FBS). Using defined binding buffer conditions the hill slope had a mean value of 1.84 with a 95% confidence interval of 1.61 to 2.07 (N=6). The $EC_{50}$ values had a mean of $2.5 \times 10^{-10}$ molar with a 95% confidence interval of $3.3 \times 10^{-10}$ molar to $1.9 \times 10^{-10}$ molar.

The assay was also performed several times (n=5) using a slight modification of the protocol described in the materials and methods. In this protocol the plate was blocked using Superblock (Pierce Chemical Company) according to the manufacturer's recommendations. In addition all washes were performed using only TBS containing 0.05% tween 20. Under these conditions the hill slope (mean 2.0; 95% confidence interval; 1.7 to 2.3) and the $EC_{50}$ (mean $2.36 \times 10^{-10}$ molar; 95% confidence interval $2.5 \times 10^{-10}$M. to $2.23 \times 10^{-10}$M.) did not differ significantly from the values obtained in the original assay. The mean values for the hill slope and $EC_{50}$ for assays performed in binding buffer containing pooled rat sera, also did not differ significantly from the numbers obtained in either of the defined buffer conditions. In fact, this assay has been used successfully to quantify the VEGF levels produced by A673 cells in culture (data not shown). The r value for the curve is typically 0.99 under all conditions described and the limit of detection for human VEGF varied between 4 and 30 picomolar depending upon the individual assay.

Initial Error analyses have been performed using defined buffers. To accomplish this each of the nine dilutions of the standard curve were randomly distributed on a microtiter plate revealed an intra-assay relative standard deviations as low as 5% could be achieved.

EXAMPLE 2 hCG ELONA hCG is a glycoprotein which stimulates the production of progesterone during the early phase of pregnancy. Although the presence of elevated levels of hCG is widely used as a marker for pregnancy, hCG levels can also be sued for other clinical applications. Abnormally low serum levels of hCG are often observed in individuals prone to spontaneous abortions. Changes in hCG levels during pregnancy may indicate ectopic pregnancies, whereas significantly high levels of hCG in the very early stage of pregnancy may help in detecting multiple pregnancies. hCG levels are also known to be reliable markers for tropoblastic tumors and testicular carcinoma. A SELEX-derived nucleic acid ligand which binds hCG as described in concurrently filed U.S. patent application Ser. No. 08/488,402 filed Jun. 7, 1995 entitled "High Affinity Oligonucleotide Ligands to Chorionic Gonadotropin Hormone and related Glycoprotein Hormones," can act as a capture molecule in a sandwich-type ELONA assay.

A. Materials and Methods

Many of the materials and methods are similar to those employed in Example 1 and 3.

hCG antibody and detection system

The hCG-specific monoclonal antibody 152 and ELISA kit for hCG detection were purchased from BioClin.

Capture molecule

An RNA ligand that binds to hCG with high affinity was used as the capture molecule. The RNA ligand was identified as described in concurrently filed U.S. patent application Ser. No. 08/488,408, filed Jun. 7, 1995 entitled "High Affinity Oligonucleotide Ligands to Chorionic Gonadotropin Hormone and related Glycoprotein Hormones", which is incorporated herein by reference in its entirety. The RNA ligand was termed H-42 and had the following sequence 5'-GGGAGGAC GAUGCGGACAAGGGCCUGAGU-GUGGAGGGCACGUGGAGGGGACUGGCCAGACG ACUCGCCCGA-3' (SEQ ID NO: 2). All cytosines and uridines are modified at the 2'-position with an $NH_2$ group in place of the OH group. The RNA ligand was derivatized with GDP-β-S at the 5'-end were synthesized by transcription in vitro in a reaction mixture containing a 10-fold excess of GDP-β-S over GTP (from Calbiochem). RNA was gel purified, resuspended in 100 mM triethylammonium acetate buffer (pH 7.5), and reacted with a ten-fold excess of DTT at 37° C. for 30 min. DTT-treated RNA was then incubated with 100-fold excess of iodoacetyl-LC-biotin (from Pierce Chemicals) in dimethyl formamide for two hr at 37° C. The excess unreacted iodoacetyl-LC-biotin was inactivated by reacting with 10 mM DTT. The biotinylated RNA was separated from the unreacted iodoacetyl-LC-biotin by flowing through an Ultrafree-MC filter (30 kD MW cut off; Millipore). RNA retained on the filter was washed with TEM buffer and recovered.

B. ELONA Procedure

Biotinylated RNA in TEM buffer (~0.5–1 nmole/200 µL per well) was incubated in streptavidin-coated 96 well microtiter plates (from BioClin) for 1–2 hr at ambient temperature. Unbound RNA was removed by washing the wells with several volumes of TEM buffer. The wells were then blocked with 1% polyvinyl alcohol in TEM. The appropriate solution containing either control hormone solution or test solution was added to the RNA-coated wells and incubated for 2 hr. The unbound hormone was removed by washing several times with TEM buffer containing 0.05% Tween-20. Horseradish peroxidase (HRP)-labeled detection antibody from the hCG detection kit (ELISA kit from BioClin) was added and the subsequent steps were performed according to the manufacturer's instructions. The absorbance at 450 nm was determined in a Biotek plate reader.

Figure 2:
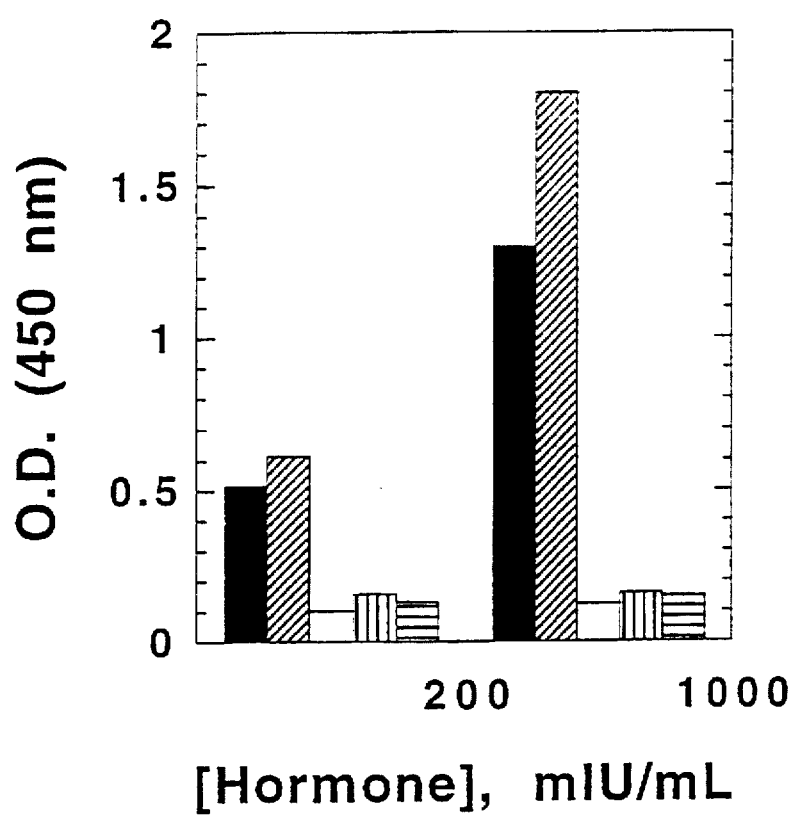
FIG. 2 shows hCG detection by ELONA. Solid bars represent the results obtained with the full-length H-42 RNA ligand (SEQ ID NO: 2) to capture hCG. Stippled bars show the results obtained with an antibody-based commercial assay for hCG detection. Open bars and the vertical lines indicate the results obtained with a nonspecific biotinylated ssDNA to capture hCG and hLH, respectively. Horizontal lines indicate the results obtained with H-42-attached wells to detect hLH. The detector molecule was a horseradish peroxidase labeled anti-hCG antibody from a commercial kit obtained from BioClin.

FIG. 2 shows a comparison of the results obtained with an RNA-based sandwich assay (stippled bars) and an antibody-based commercially available assay kit (solid bars). As in the commercial kit, the intensity of color generated in the RNA-based assay is directly proportional to the amount of hCG added, indicating that the RNA ligand serves well as a capturing ligand. With some optimization of the assay, the RNA-based ELONA allowed the detection of hCG down to 200 mIU (340 pM) in TEM buffer. However, with hCG-spiked urine samples gave high background, suggesting that additional optimization of the assay may be required. Due to the specificity of the detector antibody, neither test generated a good positive signal when hLH was used in place of hCG (bars with vertical and horizontal stripes). No detectable signal was observed when a nonspecific ssDNA sequence biotinylated at the 5'-end was used as a control (open bars).

EXAMPLE 3 hTSH ELONA hTSH is a glycohormone whcih stimulates the synthesis of thyroid hormones. Measurements of serum hTSH levels are important in the diagnosis of both pituitary and thyroid disorders such as hyperthyroidism and hypothyroidism. A SELEX-derived nucleic acid ligand which binds hTSH as described in concurrently filed U.S. patent application Ser. No. 08/488,402 filed Jun. 7, 1995 entitled "High Affinity Oligonucleotide Ligands to Chorionic Gonadotropin Hormone and related Glycoprotein Hormones" can act as a capture molecule in a sandwich-type ELONA assay.

A. Materials and Methods

Many of the materials and methods are similar to those employed in Examples 1 and 2. Deoxyoligonucleotides were synthesized by standard cyanoethyl phosphoramidite chemistry. 2'-$NH_2$-modified UTP and CTP were synthesized by known methods. hTSH ($M_r$=27,700; 9 IU (International Units)/mg); hLH ($M_r$=35,500), hFSH ($M_r$=38,250) were from Becton Dickinson (Research Triangle Park, N.C.). hCG ($M_r$=42,000; 14,000 IU/mg) was from Vitro Diagnostics (Littleton, Colo.). An ELISA kit for hTSH detection and anti-hTSH monoclonal antibody (clone 183) were purchased from BioClin, Inc. (St. Louis, Mo.). The α-subunit ($M_r$=14,900) and the β-subunit ($m_r$=30,000) of hTSH were obtained from Calbiochem (LaJolla, Calif.).

Capture molecule

An RNA ligand that binds to hTSH with high affinity was used as the capture molecule. The RNA ligand was identified as described in concurrently filed U.S. patent application Ser. No. 08/488,402, filed Jun. 7, 1995 entitled "High Affinity Oligonucleotide Ligands to Chorionic Gonadotropin Hormone and related Glycoprotein Hormones", which is incorporated herein by reference in its entirety. The RNA ligand was term T-15 and had the following sequence 5'-GGGAGGACG AUGCGGAUGUUGGCAG-CAGGGUCCGACGGCGUAACCUUGC-CAGCUGCAGAC GACUCGCCCGA-3' (SEQ ID NO: 3). All cytosines and uridines are modified at the 2'-position with an $NH_2$ group in place of the OH group. The RNA ligandwas derivatized with GDP-β-S at the 5'-end were synthesized by transcription in vitro in a reaction mixture containing a 10-fold excess of GDP-β-S over GTP (from Calbiochem). RNA was gel purified, resuspended in 100 mM triethylammonium acetate buffer (pH 7.5), and reacted with a ten-fold excess of DTT at 37° C. for 30 min. DTT-treated RNA was then incubated with 100-fold excess of iodoacetyl-LC-biotin (from Pierce Chemicals) in dimethyl formamide for two hr at 37° C. The excess unreacted iodoacetyl-LC-biotin was inactivated by reacting with 10 mM DTT. The biotinylated RNA was separated from the unreacted iodoacetyl-LC-biotin by passing through an Ultrafree-MC filter (30 kD MW cut off; Millipore). RNA retained on the filter was washed with TEM buffer and recovered.

B. ELONA Procedure

Biotinylated RNA in TEM buffer was incubated in streptavidin-coated 96 well microtiter plates (~0.5–1 nmole/ 200 μL per well) for 1–2 hr at ambient temperature. Unbound RNA was removed by washing the wells with several volumes of TEM buffer. The wells were then blocked with 1% polyvinyl alcohol in TEM. hTSH, suspended in TEM buffer, was added to the RNA-coated wells and incubated for 2 hr. The unbound hormone was removed by washing several times with TEM buffer containing 0.05% Tween-20. Horseradish peroxidase (HRP)-labeled detection antibody from the hTSH detection kit (ELISA kit from BioClin) was added and the subsequent steps were performed according to the manufacturer's instructions. The absorbance at 450 nm was determined in a Biotek plate reader. The control antibody-based ELISA was performed according to the manufacturer's instructions.

Figure 3:
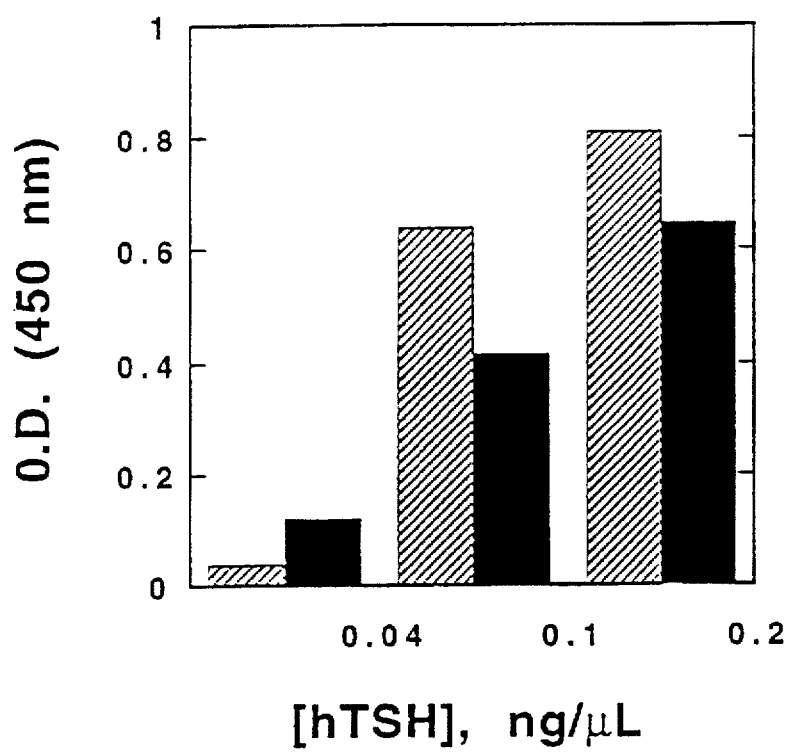
FIG. 3 shows hTSH detection by ELONA. Stippled bars represent the results obtained with the T-15 RNA ligand (SEQ ID NO: 3) to capture hTSH. Solid bars show the results obtained with a commercially available antibody-based ELISA assay (BioClin) for hTSH detection. The absorbance values shown were background corrected.

FIG. 3 shows a comparison of the results obtained with an RNA-based sandwich assay (stippled bars) and an antibody-based commercially available assay kit (solid bars). The RNA-based ELONA provided signals that were analogous to those seen with the commercially available antibody-based ELISA, indicating that nucleic acid ligand T-15 functions well as a capture molecule for hTSH.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:1:

```
ACCCTGATGG TAGACGCCGG G                                    2 1
```

( 2 ) INFORMATION FOR SEQ ID NO:2:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:2:

```
GGGAGGACGA UGCGGACAAG GGCCUGAGUG UGGAGGGCAC GUGGAGGGGA       5 0

CUGGCCAGAC GACUCGCCCG A                                      7 1
```

( 2 ) INFORMATION FOR SEQ ID NO:3:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear -continued (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:3:

```
GGGAGGACGA UGCGGAUGUU GGCAGCAGGG UCCGACGGCG UAACCUUGCC        50
AGCUGCAGAC GACUCGCCCG A                                       71
```

We claim:

1. A method for detecting the presence of a target compound in a substance which may contain said target compound comprising:
   a) identifying a nucleic acid ligand from a candidate mixture of nucleic acids, said nucleic acid ligand being a ligand of said target compound, by the method comprising:
      i) contacting the candidate mixture with said target compound, wherein nucleic acids having an increased affinity to said target relative to the candidate mixture may be partitioned from the remainder of the candidate mixture;
      ii) partitioning the increased affinity nucleic acids from the remainder of the candidate mixture;
      iii) amplifying the increased affinity nucleic acids to yield a ligand-enriched mixture of nucleic acids; and
      iv) identifying said nucleic acid ligand;
   b) exposing a substance which may contain said target compound to a capture molecule which binds to said target compound;
   c) removing the remainder of said substance from said capture molecule:target compound complex;
   d) adding to said capture molecule:target compound complex a detector molecule which binds to said target compound; and
   e) detecting said capture molecule:target compound:detector molecule complex; wherein said capture molecule, said detector molecule or both comprise a nucleic acid ligand to said target compound identified by the method of step (a).

2. The method of claim 1 wherein said detector molecule comprises an enzyme.

3. The method of claim 2 wherein said detection is accomplished by the addition of a substrate which said enzyme can hydrolyze thereby producing a measurable color.

4. The method of claim 2 wherein said enzyme is selected from the group consisting of horseradish peroxidase, alkaline phosphatase, and β-galactosidase.

5. The method of claim 1 wherein said capture molecule is bound to a solid carrier.

6. The method of claim 1 wherein said target compound is a protein.

7. The method of claim 6 wherein said protein is selected from the group consisting of Vascular Endothelial Growth Factor (VEGF), Human Chorionic Gonadotropin (hCG) and Human Thyroid Stimulating Hormone (hTSH).

8. The method of claim 1 wherein said substance is a biological fluid.

9. The method of claim 8 wherein said biological fluid is selected from the group consisting of blood, plasma, serum, sputum, urine, semen, cerebrospinal fluid, bronchial aspirate, and macerated tissue.

10. The method of claim 1 wherein said detection is achieved by PCR amplification of said nucleic acid ligand.

11. The method of claim 10 wherein the primers used for PCR amplification further comprise reporter groups.

12. The method of claim 11 wherein said reporter groups are biotin or an enzyme.

13. A method for detecting the presence of a protein in a substance which may contain said protein, wherein said protein does not have the known physiological biological function of binding a nucleic acid, comprising:
   a) identifying a nucleic acid ligand from a candidate mixture of nucleic acids, said nucleic acid ligand being a ligand of said protein, by the method comprising:
      i) contacting the candidate mixture with said protein, wherein nucleic acids having an increased affinity to said protein relative to the candidate mixture may be partitioned from the remainder of the candidate mixture;
      ii) partitioning the increased affinity nucleic acids from the remainder of the candidate mixture;
      iii) amplifying the increased affinity nucleic acids to yield a ligand-enriched mixture of nucleic acids; and
      iv) identifying said nucleic acid ligand;
   b) exposing a substance which may contain said protein to a capture molecule which binds to said protein;
   c) removing the remainder of said substance from said capture molecule:protein complex;
   d) adding to said capture molecule:protein complex a detector molecule which binds to said protein; and
   e) detecting said capture molecule:protein:detector molecule complex, wherein said capture molecule, said detector molecule or both comprise a nucleic acid ligand to said protein.

14. The method of claim 13 wherein said detector molecule comprises an enzyme.

15. The method of claim 13 wherein said capture molecule is bound to a solid carrier.

16. The method of claim 13 wherein said protein is selected from the group consisting of Vascular Endothelial Growth Factor (VEGF), Human Chorionic Gonadotropin (hCG) and Human Thyroid Stimulating Hormone (hTSH).

17. The method of claim 13 wherein said substance is a biological fluid.

18. The method of claim 17 wherein said biological fluid is selected from the group consisting of blood, plasma, serum, sputum, urine, semen, cerebrospinal fluid, bronchial aspirate and macerated tissue.

19. The method of claim 14 wherein said detection is accomplished by the addition of a substrate which said enzyme can hydrolyze, thereby producing a measurable color.

20. The method of claim 14 wherein said enzyme is selected from the group consisting of horseradish peroxidase, alkaline phosphatase and β-galactosidase.

21. The method of claim 13 wherein said detection is achieved by PCR amplification of said nucleic acid ligand.

22. The method of claim 21 wherein the primers used for PCR amplification further comprise reporter groups.

23. The method of claim 22 wherein said reporter groups are biotin or an enzyme.

* * * * *

UNITED STATES PATENT AND TRADEMARK OFFICE
CERTIFICATE OF CORRECTION

PATENT NO. : 5,789,163
DATED : August 4, 1998
INVENTOR(S) : Dan W. Drolet, Sumedha D. Jayasena and Larry Gold It is certified that error appears in the above-identified patent and that said Letters Patent is hereby corrected as shown below:

Immediately following column 14, line 15, please replace the Sequence Listing with the following Sequence Listing:

```
       SEQUENCE LISTING
(1)    GENERAL INFORMATION:
       (i) APPLICANT:    DROLET, DAN
                         JAYASENA, SUMEDHA
                         GOLD, LARRY
       (ii) TITLE OF INVENTION:      ENZYME LINKED OLIGONUCLEOTIDE ASSAYS
                                     (ELONAS) (as amended)
       (iii) NUMBER OF SEQUENCES: 3
       (iv) CORRESPONDENCE ADDRESS:
            (A)   ADDRESSEE: Swanson & Bratschun, L.L.C.
            (B)   STREET: 8400 E. Prentice Avenue, Suite 200
            (C)   CITY: Englewood
            (D)   STATE: Colorado
            (E)   COUNTRY:   USA
            (F)   ZIP: 80111
       (v)  COMPUTER READABLE FORM:
            (A)   MEDIUM TYPE: Diskette, 3 1/2 diskette, 1.44 MB
            (B)   COMPUTER: IBM pc compatible
            (C)   OPERATING SYSTEM: MS-DOS
            (D)   SOFTWARE: WordPerfect 8.0
       (vi) CURRENT APPLICATION DATA:
            (A)   APPLICATION NUMBER: 08/487,425
            (B)   FILING DATE: 07-June 1995
            (C)   CLASSIFICATION:
       (vii)PRIOR APPLICATION DATA:
            (A)   APPLICATION NUMBER: 07/714,131
            (B)   FILING DATE: 10-JUNE-1991
       (vii)PRIOR APPLICATION DATA:
            (A)   APPLICATION NUMBER: 07/536,428
            (B)   FILING DATE: 11-JUNE-1990
```

UNITED STATES PATENT AND TRADEMARK OFFICE
CERTIFICATE OF CORRECTION

PATENT NO. : 5,789,163
DATED : August 4, 1998
INVENTOR(S) : Dan W. Drolet, Sumedha D. Jayasena and Larry Gold It is certified that error appears in the above-identified patent and that said Letters Patent is hereby corrected as shown below:

```
          (vii) PRIOR APPLICATION DATA:
                (A)   APPLICATION NUMBER: 07/964,624
                (B)   FILING DATE: 21-OCTOBER-1992
          (vii) PRIOR APPLICATION DATA:
                (A)   APPLICATION NUMBER: 08/234,997
                (B)   FILING DATE: 28-APRIL-1994
         (viii) ATTORNEY/AGENT INFORMATION:
                (A)   NAME: Barry J. Swanson
                (B)   REGISTRATION NUMBER: 33,215
                (C)   REFERENCE/DOCKET NUMBER: NEX37
           (ix) TELECOMMUNICATION INFORMATION:
                (A)   TELEPHONE: (303) 793-3333
                (B)   TELEFAX: (303) 793-3433
  (2)     INFORMATION FOR SEQ ID NO:1:
          (i)   SEQUENCE CHARACTERISTICS:
                (A)   LENGTH: 21 base pairs
                (B)   TYPE: nucleic acid
                (C)   STRANDEDNESS: single
                (D)   TOPOLOGY:    linear
          (ii)  MOLECULAR TYPE: RNA
          (ix)  FEATURE:
                (D)   OTHER INFORMATION: All C's are 2'-NH$_2$ cytosine
          (ix)  FEATURE:
                (D)   OTHER INFORMATION: All U's are 2'-NH$_2$ uracil
          (xi)  SEQUENCE DESCRIPTION: SEQ ID NO:1:
  ACCCUGAUGG UAGACGCCGG G                                              21
```

UNITED STATES PATENT AND TRADEMARK OFFICE
CERTIFICATE OF CORRECTION

PATENT NO. : 5,789,163

DATED : August 4, 1998

INVENTOR(S) : Dan W. Drolet, Sumehda D. Jayasena and Larry Gold

It is certified that error appears in the above-identified patent and that said Letters Patent is hereby corrected as shown below:

```
(2)    INFORMATION FOR SEQ ID NO:2:
       (i)    SEQUENCE CHARACTERISTICS:
              (A)    LENGTH: 71 base pairs
              (B)    TYPE: nucleic acid
              (C)    STRANDEDNESS: single
              (D)    TOPOLOGY:   linear
       (ii)   MOLECULAR TYPE: RNA
       (ix)   FEATURE:
              (D)    OTHER INFORMATION: All C's are 2'-NH₂ cytosine
       (ix)   FEATURE:
              (D)    OTHER INFORMATION: All U's are 2'-NH₂ uracil
       (xi)   SEQUENCE DESCRIPTION: SEQ ID NO:2:
```

GGGAGGACGA UGCGGACAAG GGCCUGAGUG UGGAGGGCAC GUGGAGGGA       50
CUGGCCAGAC GACUCGCCCG A                                    71

UNITED STATES PATENT AND TRADEMARK OFFICE
CERTIFICATE OF CORRECTION

PATENT NO. : 5,789,163
DATED : August 4, 1998
INVENTOR(S): Dan W. Drolet, Sumehda D. Jayasena and Larry Gold It is certified that error appears in the above-identified patent and that said Letters Patent is hereby corrected as shown below:

```
(2)    INFORMATION FOR SEQ ID NO:3:
       (i)    SEQUENCE CHARACTERISTICS:
              (A)    LENGTH: 71 base pairs
              (B)    TYPE: nucleic acid
              (C)    STRANDEDNESS: single
              (D)    TOPOLOGY:   linear
       (ii)   MOLECULAR TYPE: RNA
       (ix)   FEATURE:
              (D)    OTHER INFORMATION: All C's are 2'-NH₂ cytosine
       (ix)   FEATURE:
              (D)    OTHER INFORMATION: All U's are 2'-NH₂ uracil
       (xi)   SEQUENCE DESCRIPTION: SEQ ID NO:3:
GGGAGGACGA UGCGGAUGUU GGCAGCAGGG UCCGACGGCG UAACCUUGCC      50
AGCUGCAGAC GACUCGCCCG A                                    71
```

Signed and Sealed this

Eighth Day of December, 1998

Attest:

BRUCE LEHMAN

Attesting Officer

Commissioner of Patents and Trademarks